United States Patent [19]

Scardera et al.

[11] 4,207,421
[45] Jun. 10, 1980

[54] BIODEGRADABLE, ALKALI STABLE, NON-IONIC SURFACTANTS

[75] Inventors: Michael Scardera, Hamden; Frank R. Grosser, Bethany, both of Conn.

[73] Assignee: Olin Corporation, New Haven, Conn.

[21] Appl. No.: 27,698

[22] Filed: Apr. 6, 1979

Related U.S. Application Data

[63] Continuation-in-part of Ser. No. 853,607, Nov. 21, 1977, abandoned.

[51] Int. Cl.² ............... C07C 43/04; B01F 17/00; B01F 17/42; C11D 1/72
[52] U.S. Cl. .................. 568/625; 568/618; 252/170; 252/351
[58] Field of Search ................. 568/625, 618

[56] References Cited

U.S. PATENT DOCUMENTS 3,539,519  11/1970  Weimer .................. 568/625

FOREIGN PATENT DOCUMENTS 922252  12/1959  United Kingdom .................. 568/625
950844   2/1964  United Kingdom .................. 568/625

*Primary Examiner*—Howard T. Mars
*Attorney, Agent, or Firm*—William A. Simons; Thomas P. O'Day

[57] ABSTRACT

Biodegradable, alkali stable, non-ionic surfactants are disclosed which feature the formula:

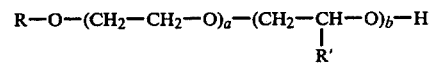

wherein R is a linear, alkyl hydrocarbon radical having an average of from 16 to 18 carbon atoms; R' is methyl or ethyl; a has an average value of 9 to 15 and b has an average value of 3 to 5; the ratio of a:b being from 2.7:1 to 3.5:1.

10 Claims, No Drawings

BIODEGRADABLE, ALKALI STABLE, NON-IONIC SURFACTANTS

This application is a continuation-in-part of co-pending Application Ser. No. 853,607, filed Nov. 21, 1977 now abandoned.

Current environmental awareness requires that surfactant compositions be biodegradable (i.e., capable of ready decomposition by bacteria or other organisms). While the surface active agent art is replete with disclosures of various compositions displaying a wide variety of properties, some difficulty has been encountered in accomplishing biodegradability while maintaining other desirable surfactant characteristics. Included among well-known surfactants are alkylene oxide condensation products. These are commonly prepared by the reaction of an organic compound having a reactive hydrogen atom with an alkylene oxide, such as ethylene oxide, propylene oxide, or higher alkylene oxides, or mixtures thereof. For example, U.S. Pat. Nos. 2,174,761; 2,674,619; and 2,677,700 all show surfactant compositions prepared by the addition of propylene oxide and ethylene oxide to reactive hydrogen compounds. However, as noted in U.S. Pat. No. 3,956,401, it is now appreciated that biodegradability of the surfactant product is detrimentally affected by any branching in the reactive hydrogen compound base. Accordingly, the reactive hydrogen compound should be linear, or at least substantially linear with essentially no branching.

U.S. Pat. No. 3,340,309, to Weipert, depicts biodegradable, low foaming, alkylene oxide condensation products prepared by condensing propylene oxide with a condensation product of ethylene oxide and a mixture of straight chain aliphatic alcohols. The mixture of alcohols contains specified proportions of various such alcohols ranging from 8 to 20 atoms. Another U.S. Pat. No. 3,770,701, to Cenker et al, relates to biodegradable, non-ionic surfactants made by condensing an aliphatic straight chain alcohol having 8 to 22 carbon atoms with a mixture of ethylene oxide and propylene oxide within required weight and ratio ranges.

A surfactant product has now been discovered, according to the present invention, which is formulated by condensing a linear aliphatic alcohol, or a blend of such alcohols, having an average chain length of 16 to 18 carbon atoms, with ethylene oxide and then propylene or butylene oxide as a capping block. Propylene oxide is preferred an an end cap. An alkylene oxide adduct is formed having about 9 to about 15 moles of ethylene oxide and about 2 to about 5 moles of capping alkylene oxide per mole of alcohol base. More preferably, the adduct contains about 9.5 to about 11.0 moles of ethylene oxide and about 2.5 to about 4.0 moles of capping alkylene oxide. The amount of alkylene oxide in the capping block is dependent on the amount of ethylene oxide utilized in the initial block, since the ratio of ethylene oxide to the capping alkylene oxide is maintained at about 2.7:1 to about 3.5:1, preferably, about 2.9:1 to about 3.3:1. The final molecular weight of the surfactant ranges from about 835 to 1215. Preferably, the molecular weight is about 850 to about 950.

Basically, the alkylene oxide adduct surfactants of the present invention consist of three components—an aliphatic linear alcohol, ethylene oxide, and a capping alkylene oxide. The alcohol serves as the hydrophobic, oil-soluble portion of the surfactant. The ethylene oxide block is the hydrophilic, water-soluble element of the surfactant; and, the use of greater proportions of the ethylene oxide favors production of surfactants of higher foaming characteristics. However, the ethylene oxide block is susceptible to degradation in alkaline compositions. Such instability renders such surfactants incompatible in various compositions used in industrial, household, and institutional applications. To promote alkali stability, the ethylene oxide block is capped with propylene or butylene oxide. This capping block, however, also induces low foaming tendency and hydrophobicity.

In seeking to enhance the alkali stability of an alkylene oxide adduct surfactant, the increased proportion of capping alkylene oxide that must be employed tends to reduce the solubility and foaming properties of the product to such an extent that it is difficult to produce a soluble surfactant compatible in alkaline compositions yet featuring sufficient foaming properties for use in applications where foaming is necessary or at least aesthetically desirable.

The prior art generally has regarded the use of linear aliphatic alcohols having an average of 16 to 18 carbon atoms to be impracticable for the production of useful surfactants. The chain length of the alcohol normally causes the product to be too hydrophobic for effective utility (for example, see U.S. Pat. No. 3,340,309, Example IV).

It has now been discovered, however, that a surfactant exhibiting advantageous alkali stability can be prepared from block alkoxylation of a linear aliphatic alcohol, or a blend of such alcohols, having an average of 16 to 18 carbon atoms in the chain, using critical proportions of ethylene oxide and propylene or butylene oxide, so as to produce a surfactant that is biodegradable, water soluble, and features sustained moderate to high foaming. It is theoretically ventured that the favorable properties of these novel surfactants are achieved because the chain length of the alcohol, 16 to 18 carbons, tends to bolster alkali stability. Accordingly, although an amount of ethylene oxide must be used to offset the hydrophobicity of this relatively long chain alcohol base, the critical amount of alkylene oxide cap, necessary to ensure alkali stability, is less than would be expected. Increased chain length of the alcohol tends to make the surfactant hydrophobic and water insoluble; the proportion of capping alkylene oxide further favors hydrophobicity. The present unexpected discovery has accomplished the use of critical amounts of ethylene oxide and alkylene oxide capping which succeeds in achieving alkali stability of the surfactant without imparting insolubility or low foaming tendency or foam instability.

More particularly, the surfactant product of the present invention has the following formula:

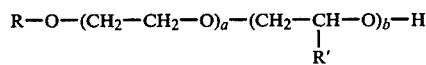

wherein R is a linear alkyl hydrocarbon having an average of about 16 to 18 carbon atoms; R' is methyl or ethyl; a has an average value of 9 to 15; b has an average value of 3 to 5; the ratio of a:b being from 2.7:1 to 3.5:1.

As set forth above, the R group, representing the residue of the alcohol reactant, is substantially linear, with essentially no branching. This linearity is vital to the biodegradability of the surfactant product. However, due to the nature of the process by which the alcohol reactant is made, some small amounts of branched chain alcohols may be present. Generally though, the presence of such branched chain alcohols in amounts less than about 15% of the total alcohol content by weight will not seriously adversely affect the overall properties of the final product. The number of carbon atoms, 16 to 18, referred to for R, is an average number, since commercial grade alcohols generally are a mixture of 16C and 18C alcohols. For example, Continental Oil's "Alfol 1618", a well-known commercial mixture, is a blend of less than about 2% 12C and 14C, about 54% to 64% 16C, about 25% to 35% 18C, and less than about 5% 20C linear alcohols, with an average hydroxyl number of about 210–223.

The values of a and b actually are average numbers and are determined by the weight of each particular reactant used to formulate the composition.

The surfactant compositions of the present invention may be prepared using any of the well-known methods of condensing an alkylene oxide with an alcohol. Such methods are described, for example, in U.S. Pat. No. 2,677,700 at column 6, in U.S. Pat. No. 3,340,309 at column 3, and "Nonionic Surfactants"—Schick (1967) at page 102. In general, the compounds may be prepared by reacting a primary, linear, monohydric alcohol having from 16 to 18 carbon atoms with ethylene oxide, in the desired amounts, at an elevated temperature (in the range of about 140° C. to 200° C., preferably about 160°–180° C.) in the presence of about 0.005% to 1.0%, based on the alcohol weight, of alkaline catalysts, such as salts or hydroxides of the alkali metals or alkaline earth metals. The preferred catalyst is KOH. Subsequent to the ethylene oxide addition, the ethoxylated product is condensed with propylene or butylene oxide, preferably propylene oxide, using the same type of catalyst and reaction conditions, to obtain the final surfactant product.

The surfactant products of the present invention are biodegradable, water soluble, moderate to high sustained foaming, and stable on dry caustic. Such advantageous properties make these surfactants useful in various applications, in particular alkaline compositions, such as detergent formulations, as wetting, washing, dispersing, etc., agents in the textile, leather, paper, paint, pharmaceutical and cosmetic industries, etc., as well as for household applications.

The following examples are provided to further illustrate the invention. All parts and percentages are by weight unless otherwise specified.

SURFACTANT FORMULATION

EXAMPLE 1

Into a three-necked, 500 ml round bottom flask fitted with a dropping funnel, nitrogen inlet, thermometer, stirrer, dry ice condenser and vent, 79.8 g (0.3 mole) of "Alfol 1618" (a blend of straight chain aliphatic alcohols having an average carbon chain length of 16–18C, primarily consisting of 16 carbon and 18 carbon alcohols) and 0.4 g potassium hydroxide (0.007 mole, 0.5% based on the alcohol weight) were added. Under a nitrogen atmosphere, 138.6 g of ethylene oxide was introduced dropwise to the alcohol at a temperature of 160°–170° C. Upon completion of the ethylene oxide addition, 63.2 g of propylene oxide (1.09 moles) is then placed in the dropping funnel and added to the reaction mixture (an alcohol—ethylene oxide adduct) dropwise at 150°–170° C. After propylene oxide addition, the reaction product was stirred an additional half hour at reaction temperature and then it was allowed to cool and the potassium hydroxide was neutralized with acetic acid. The product weighed 281.8 g. The molecular weight of the final product was determined to be about 939 with an alcohol—ethylene oxide—propylene oxide ratio of 1.0:10.5:3.6.

EXAMPLES 2 AND 3

The procedure of Example 1 was repeated for Examples 2 and 3, except that varying amounts of ethylene oxide and capping propylene oxide were utilized.

PHYSICAL AND SURFACE PROPERTIES DETERMINATION

EXAMPLES 1, 2 AND 3

To illustrate the favorable surfactant properties of the products of Examples 1, 2 and 3, the following tests were conducted, with results listed in Table A.

"Cloud Point" is an indication of water solubility. A 1% aqueous solution of the surfactant is heated until a point is reached where the surfactant begins to separate out, causing the solution to become turbid or cloudy. This is the "Cloud Point".

"Surface Tension" is the force related to the intermolecular attraction at a liquid-air interface. This property indicates the tendency of a liquid to spread or wet solid surfaces. (Per ASTM D 1331-56)

"Interfacial Tension" is the force related to the intermolecular attraction of a liquid-liquid or liquid-solid interface. This property is indicative of effective emulsification; bubble, film and foam formation and behavior; cleaning of fabrics; ore flotation; adhesives; etc. (Per ASTM D 1331-56)

"Draves Wetting Time" denotes the time required to wet a 5 g cotton skein in an aqueous solution of surfactant. This property is important to textile processing utility. (Per AATCC Method 17-1952)

"Ross-Miles Foam Height" is a measure of the foam height generated initially and remaining after five minutes in a surfactant solution. This test indicates both foaming tendency (low-moderate-high) and foam stability. (Per ASTM Method D 1173-53)

"Caustic Compatibility" is a determination of surfactant alkali stability. One gram of the surfactant spread over 20 g of sodium hydroxide pellets is sealed in a four-ounce bottle. Any discoloration of the pellets after storage at 25° C. for 48 hours is noted. Lack of discoloration is an indication of alkali stability.

As Table A illustrates, the surfactant product of of the present invention features good water solubility, as well as favorble wetting and emulsification capability. The Ross-Miles test results show that the surfactant achieves moderate to high initial foaming and adequately maintains such foam height. Stability with alkali also is demonstrated.

Table A

| | Physical and Surface Properties | | |
|---|---|---|---|
| | Example 1 | Example 2 | Example 3 |
| "Alfol 1618" Alcohol | 79.8 g (0.3 m) | 39.8 g (0.15 m) | 79.6 g (0.3 m) |
| Potassium Hydroxide | 0.4 g (0.007 m) | 0.2 g (0.0035 m) | 0.4 g (0.007 m) |

Table A-continued

| Physical and Surface Properties | Example 1 | Example 2 | Example 3 |
| --- | --- | --- | --- |
| Ethylene Oxide | 138.6 g (3.15 m) | 64.1 g (1.46 m) | 134.4 g (3.05 m) |
| Propylene Oxide | 63.2 g (1.09 m) | 24.4 g (0.42 m) | 54.2 g (0.93 m) |
| Molecular Weight | ~939 | ~854 | ~890 |
| Alcohol: EO:PO Ratio | 1:10.5:3.6 | 1:9.7:2.8 | 1:10.1:3.1 |
| Cloud Point, °C., 1% Solution | 54 | 58.5 | 57.5 |
| Surface Tension, dynes/cm, 0.1% | 31 | 31 | 33 |
| Interfacial Tension, dynes/cm, 0.1% | 5 | 6 | 7 |
| Draves Wetting Time, Secs. 0.25% @ 25° C. | 115 | 151 | 136 |
| Ross Miles Foam Height, mm Initial/After 5 Minutes @ 25° C. | 105/85 | 110/75 | 115/75 |
| Caustic Compatibility | Stable | Stable | Stable |

EXAMPLE 4 AND COMPARATIVE EXAMPLE 5

Following the general procedure as outlined in Example 1, two additional surfactants were formulated. The surfactant of Example 4 was based on a blend of $C_{16-18}$ straight chain aliphatic alcohols ("Alfol 1618") to which ethylene oxide and propylene oxide was added in successive blocks to result in an adduct featuring an alcohol:EO:PO ratio of 1:9:3.

In Comparative Example 5, a surfactant not within the scope of the present invention is shown. This comparative surfactant has an overall composition ratio as in Example 4, i.e., an alcohol:EO:PO ratio of 1:9:3; however, the alcohol base is a straight chain aliphatic alcohol of only 12-14 carbon atoms. Such a composition is listed in British Patent No. 922,252, in the table on page 3.

Both products, Example 4 and Comparative Example 5, were tested for stability to alkali, as well as initial foaming tendency and foam stability. Both surfactants exhibited comparable resistance to caustic degradation (1 g of each surfactant was spread over 20 g of sodium hydroxide pellets and sealed in a four-ounce bottle maintained at 60° C. No discoloration was noted during periodic checks made over a period of one week.). However, a marked distinction was noted in foam characteristics as evidenced by the Ross-Miles test. The initial foam heights produced by each of the surfactants were comparable, but the vital factor of foam stability showed wide disparity. The surfactant products, tested at 25° C. and 0.25 weight percent concentration, showed the following Ross-Miles results:

| | Adducts (Moles) | Foam Height (Initial/After 5 Mins.) |
| --- | --- | --- |
| Comparative Example 5 | $C_{12-14}$OH-9EO-3PO | 115 mm/25 mm |
| Example 4 | $C_{16-18}$OH-9EO-3PO | 110 mm/75 mm |

The surfactant based on the 12-14 carbon chain alcohol would be unsuitable for a product requiring high or moderate foam characteristics, since the initial foam displays short-lived stability. Such findings of foam instability find general agreement in the above-mentioned British patent which cites surfactants, such as the subject $C_{12-14}$ alcohol based adduct, as having a "lack of foaming power".

We claim:

1. A surfactant product having the formula:

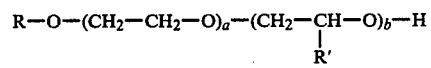

wherein R is a linear alkyl hydrocarbon radical having an average of about 16 to 18 carbon atoms; R' is an alkyl radical selected from methyl and ethyl; a is an integer having a value of about 9 to 15; b is an integer having a value of about 2 to 5; and the ratio of a:b is from 2.7:1 to 3.5:1.

2. The surfactant product of claim 1 wherein R' is methyl.

3. The surfactant product of claim 1 wherein a has a value of about 9.5 to 11.0 and b has a value of about 2.5 to 4.0.

4. The surfactant product of claim 1 wherein the ratio of a:b is about 2.9:1 to 3.3:1.

5. The surfactant product of claim 1 wherein the final molecular weight of the surfactant is about 835 to about 1215.

6. The surfactant product of claim 5 wherein the final molecular weight is about 850 to about 950.

7. The surfactant product of claim 1 wherein R is the residue of a blend of linear aliphatic alcohols having an average chain length of about 16 to 18 carbon atoms and comprising less than about 2% 12 carbon and 14 carbon alcohols, about 54% to 64% 16 carbon alcohols, about 25% to 35% 18 carbon alcohols, and less than about 5% 20 carbon alcohols.

8. The surfactant product of claim 1 wherein a has a value of about 9.5 to 11.0, b has a value of about 2.5 to 4.0, the ratio of a:b is about 2.9:1 to 3.3:1, and the final molecular weight of the surfactant is about 850 to 950.

9. The surfactant product of claim 8 wherein R' is methyl.

10. The surfactant product of claim 9 wherein R is the residue of a blend of linear aliphatic alcohols having an average chain length of about 16 to 18 carbon atoms and comprising less than about 2% 12 carbon and 14 carbon alcohols, about 54% to 64% 16 carbon alcohols, about 25% to 35% 18 carbon alcohols, and less than about 5% 20 carbon alcohols.

* * * * *